(12) United States Patent
Lai et al.

(10) Patent No.: US 10,017,394 B2
(45) Date of Patent: Jul. 10, 2018

(54) PROCESS FOR PREPARING A MOLECULAR SIEVE

(71) Applicant: ExxonMobil Chemical Patents Inc.

(72) Inventors: Wenyih F. Lai, Bridgewater, NJ (US); Nicholas S. Rollman, Hamburg, PA (US); Guang Cao, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 370 days.

(21) Appl. No.: 15/002,809

(22) Filed: Jan. 21, 2016

(65) Prior Publication Data

US 2016/0221832 A1 Aug. 4, 2016

Related U.S. Application Data

(60) Provisional application No. 62/111,730, filed on Feb. 4, 2015.

(30) Foreign Application Priority Data

Mar. 23, 2015 (EP) .................................... 15160258

(51) Int. Cl.
*C01B 39/26* (2006.01)
*B01J 29/18* (2006.01)
(Continued)

(52) U.S. Cl.
CPC ............. *C01B 39/265* (2013.01); *B01J 20/18* (2013.01); *B01J 20/2803* (2013.01); *B01J 20/28007* (2013.01); *B01J 20/28059* (2013.01); *B01J 20/28061* (2013.01); *B01J 20/28083* (2013.01); *B01J 20/3078* (2013.01); *B01J 29/18* (2013.01); *B01J 29/22* (2013.01); *B01J 29/24* (2013.01);
(Continued)

(58) Field of Classification Search
CPC ............... C01B 39/265; C01P 2004/64; C01P 2006/12; B01J 20/18; B01J 20/28007; B01J 20/28083; B01J 29/18; B01J 29/22; B01J 29/24; B01J 35/023; B01J 35/1061; B01J 35/108

See application file for complete search history.

(56) References Cited

U.S. PATENT DOCUMENTS 3,354,078 A  11/1967 Miale et al.
4,536,486 A  8/1985 Lewis
(Continued)

FOREIGN PATENT DOCUMENTS

EP  2589573  5/2013
WO  00/06492  2/2000
(Continued)

OTHER PUBLICATIONS

Selvam et al, "Synthesis and characterization of mordenite (MOR) zeolite derived from a layered silicate", Studies in Surface Science and Catalysis, (2002) pp. 407-414.*
(Continued)

*Primary Examiner* — David M Brunsman
(74) *Attorney, Agent, or Firm* — Darryl M. Tyus

(57) ABSTRACT

The present invention provides a mordenite zeolite having a mesopore surface area of greater than 30 $m^2/g$ and an average primary crystal size as measured by TEM of less than 80 nm, and methods of making the mordenite zeolite.

14 Claims, 7 Drawing Sheets

Primary crystal size distribution on Examples 6, 7 & 12

(51) Int. Cl.
*B01J 20/18* (2006.01)
*B01J 20/28* (2006.01)
*B01J 20/30* (2006.01)
*B01J 29/22* (2006.01)
*B01J 29/24* (2006.01)
*C07C 6/12* (2006.01)
*B01J 29/40* (2006.01)
*B01J 29/70* (2006.01)
*B01J 29/80* (2006.01)
*B01J 35/00* (2006.01)
*B01J 35/02* (2006.01)
*B01J 35/10* (2006.01)

(52) U.S. Cl.
CPC .............. *C01B 39/26* (2013.01); *C07C 6/12* (2013.01); *B01J 29/40* (2013.01); *B01J 29/70* (2013.01); *B01J 29/80* (2013.01); *B01J 35/002* (2013.01); *B01J 35/023* (2013.01); *B01J 35/108* (2013.01); *B01J 35/1057* (2013.01); *B01J 35/1061* (2013.01); *B01J 2229/16* (2013.01); *B01J 2229/18* (2013.01); *B01J 2229/62* (2013.01); *C01P 2004/64* (2013.01); *C01P 2006/12* (2013.01); *C07C 2529/18* (2013.01)

(56) References Cited

U.S. PATENT DOCUMENTS

| | | | |
|---|---|---|---|
| 5,077,254 | A | 12/1991 | Travers et al. |
| 5,929,296 | A | 7/1999 | Merlen et al. |
| 6,150,292 | A | 11/2000 | Merlen et al. |
| 6,359,184 | B1 | 3/2002 | Kato et al. |
| 6,465,705 | B1 | 10/2002 | Merlen et al. |
| 6,504,076 | B1 | 1/2003 | Xiao et al. |
| 6,815,570 | B1 | 11/2004 | Negiz et al. |
| 6,846,964 | B2 | 1/2005 | Xiao et al. |
| 6,867,340 | B2 | 3/2005 | Oh et al. |
| 6,936,744 | B1* | 8/2005 | Cheng ............... C07C 6/126 585/470 |
| 6,972,348 | B2 | 12/2005 | Negiz et al. |
| 7,148,391 | B1 | 12/2006 | Buchanan et al. |
| 7,273,828 | B1 | 9/2007 | Boldingh et al. |
| 7,307,034 | B2 | 12/2007 | Negiz et al. |
| 7,393,989 | B2 | 7/2008 | Negiz et al. |
| 7,419,931 | B2 | 9/2008 | Serra et al. |
| 7,485,763 | B2 | 2/2009 | Buchanan et al. |
| 7,626,064 | B1 | 12/2009 | Boldingh et al. |
| 7,687,423 | B2 | 3/2010 | Moscoso et al. |
| 9,802,181 | B2* | 10/2017 | Elia ............... B01J 29/80 |

FOREIGN PATENT DOCUMENTS

| | | |
|---|---|---|
| WO | 2009/158233 | 12/2009 |
| WO | 2014/135662 | 9/2014 |

OTHER PUBLICATIONS

Baerlocher et al., *Atlas of Zeolite Framework Types*, Elsevier, Sixth Revised Edition, 2007.

Burton et al, "On the estimation of average crystallite size of zeolites from the Scherrer equation: A critical evaluation of its application to zeolites with one-dimensional pore systems," Microporous and Mesoporous Materials, 117, pp. 75-90 (2009).

Lowell et al., *Characterization of Porous Solids and Powders: Surface Area, Pore Size and Density*, Particle Technology Series, Springer, (2004).

Lue et al., "Direct synthesis of high-silica mordenite using seed crystals", Microporous and Materials, Elsevier, vol. 76, pp. 1-7, (2004).

Miale et al. "Catalysis by Crystalline Aluminosilcates IV. Attainable Catalytic Cracking Rate Constants, and Superactivity," Journal of Catalysis, vol. 6, p. 278-287 (1966).

Olson et al., "Chemical and Physical Properties of the ZSM-5 Substitutional Series", Journal of Catalysis, vol. 61, p. 390-396, (1980).

Roberge et al., "Dealumination of zeolite beta by acid leaching: a new insight with two-dimensional multi-quantum and cross polarization $^{27}Al$ MAS NMR", Physical Chemistry Chemical Physics, pp. 3128-3135, 2002.

Scherrer, "*Bestimmung der Grösse und der inneren Struktur von Kolloidteilchen mittels Röntgenstrahlen*". Nachrichten von der Königlichen Gesellschaft der Wissenschaften zu Göttinger, Math.-Phys. Kl. 2, p. 96-100, (1918).

Walter, D. "*Primary Particles—Agglomerates—Aggregates*," in Nanomaterials (ed. Deutsche Forschungsgemeinschaft (DFG), Wiley-VCH Verlag GmbH & Co. KGaA, Weinheim, Germany. Doi: 10.1002/9783527673919, pp. 1-24 (2013).

Weisz et al., "*Superactive Crystalline Aluminosilicate Hydrocarbon Catalysts*," Journal of Catalysis, vol. 4, p. 527-529 (1965).

* cited by examiner

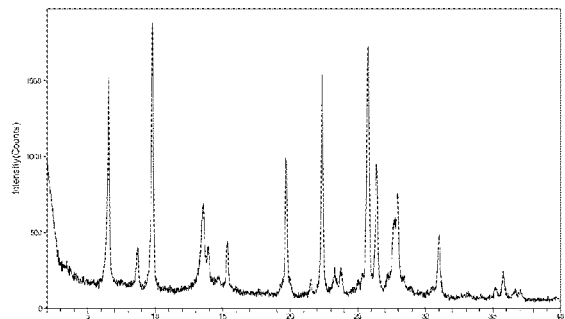
Figure 1A: XRD of Example 1
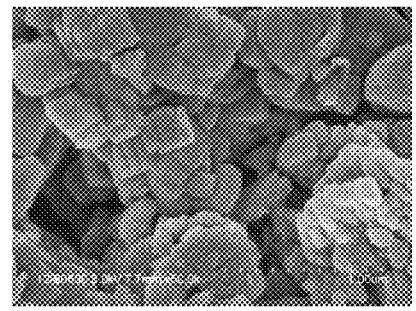
Figure 1B: SEM on Example 1
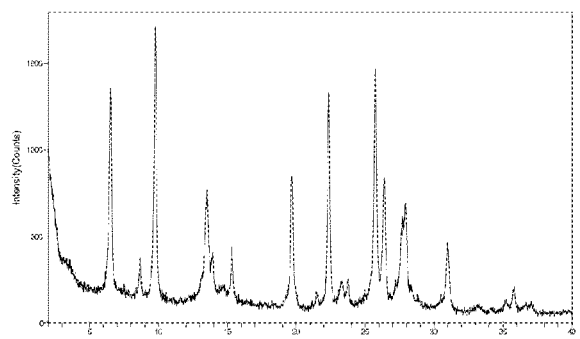
Figure 2A: XRD of Example 2
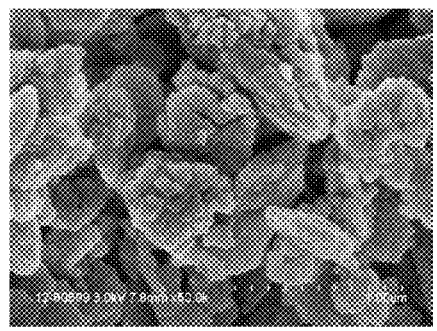
Figure 2B: SEM on Example 2
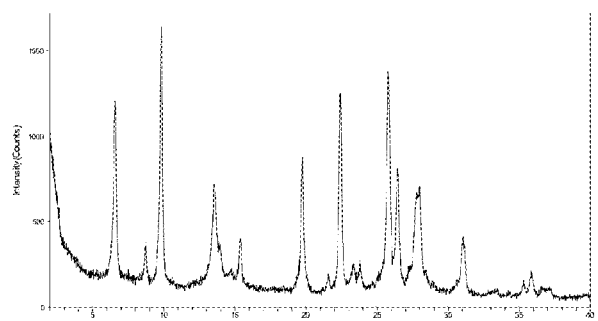
Figure 3A: XRD of Example 4
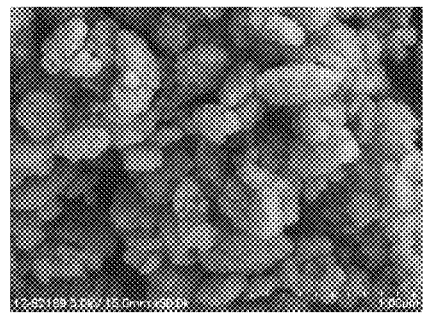
Figure 3B: SEM on Example 4

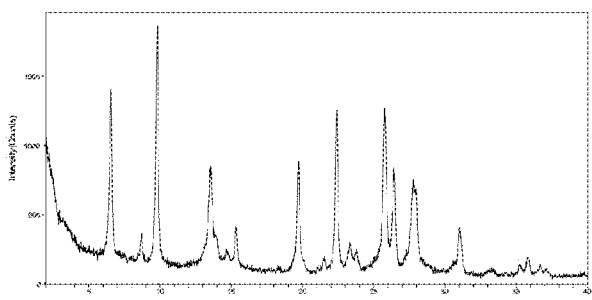
Figure 4A: XRD on Example 5
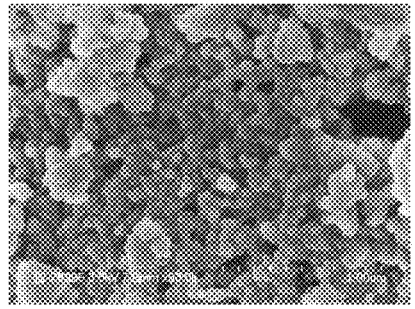
Figure 4B: SEM on Example 5
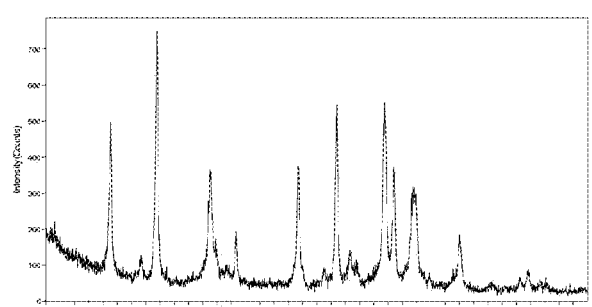
Figure 5A: XRD on Example 6
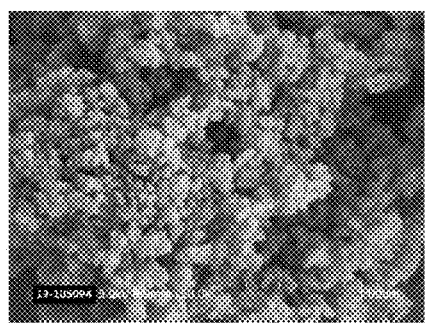
Figure 5B: SEM on Example 6
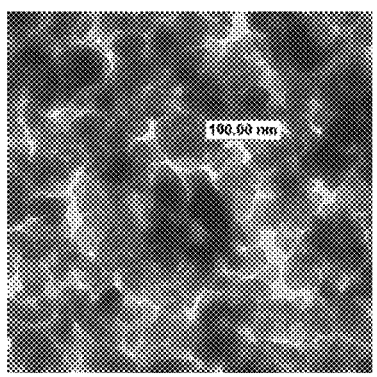
Figure 5C: TEM on Example 6

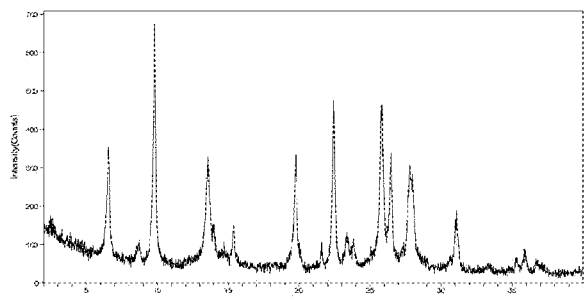
Figure 6A: XRD on Example 7
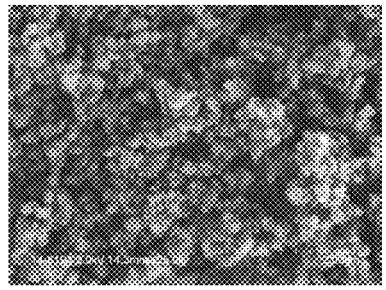
Figure 6B: SEM on Example 7
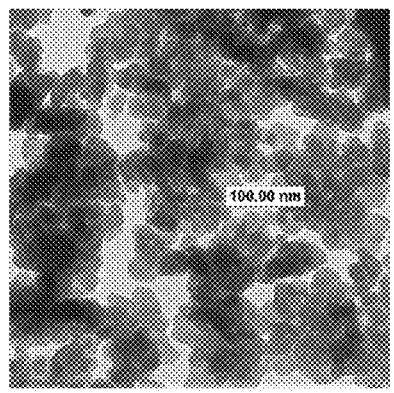
Figure 6C: TEM on Example 7
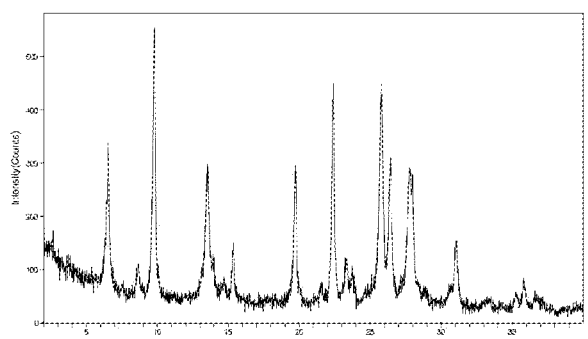
Figure 7A: XRD on Example 10
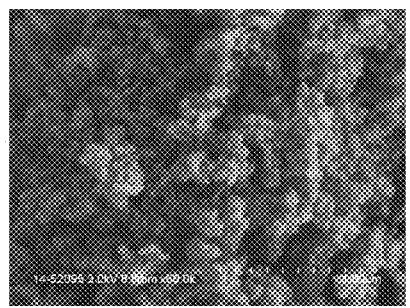
Figure 7B: SEM on Example 10

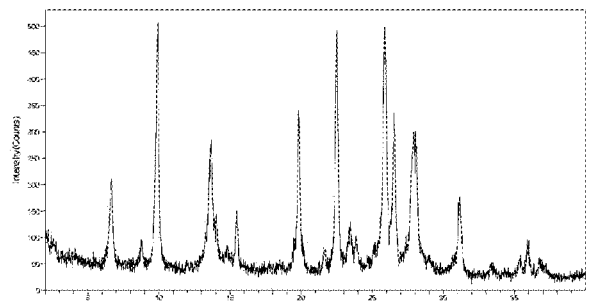
Figure 8A: XRD on Example 12
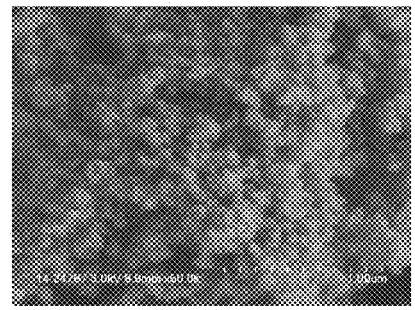
Figure 8B: SEM on Example 12
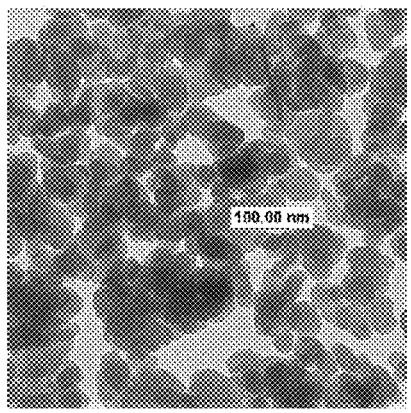
Figure 8C: TEM on Example 12
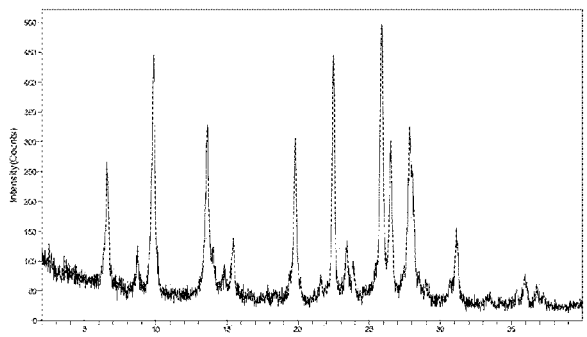
Figure 9A: XRD on Example 14
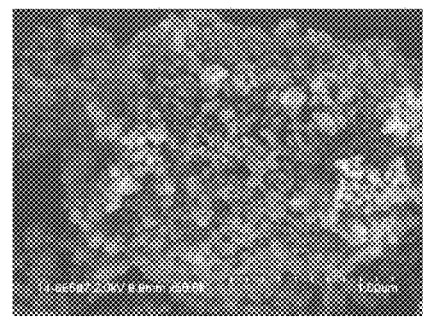
Figure 9B: SEM on Example 14

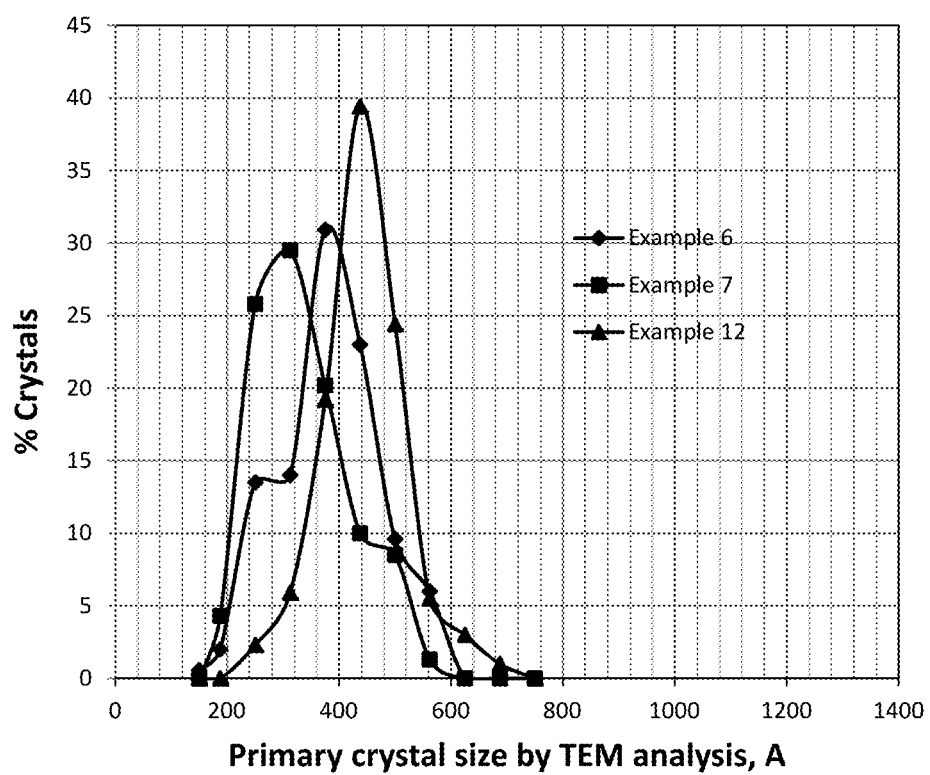
Figure 10: Primary crystal size distribution on Examples 6, 7 & 12

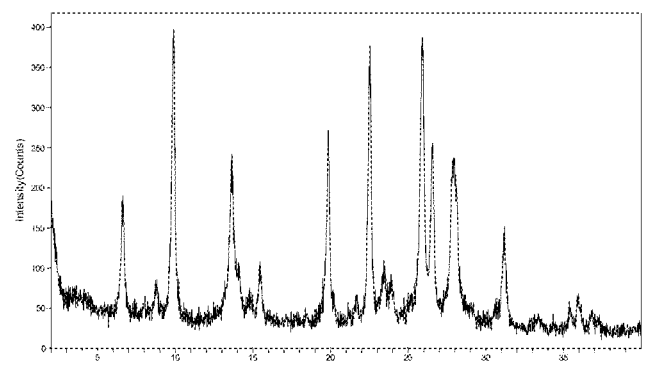
Figure 11A: XRD on Example 15
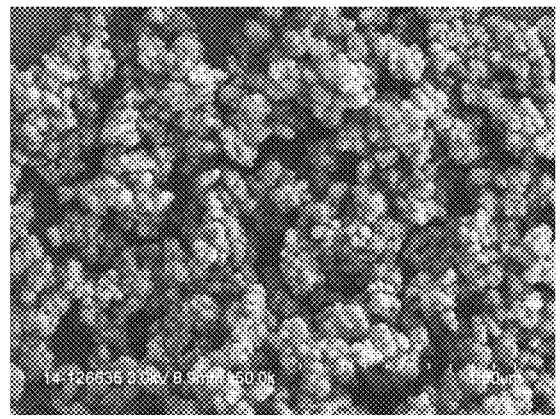
Figure 11B: SEM on Example 15

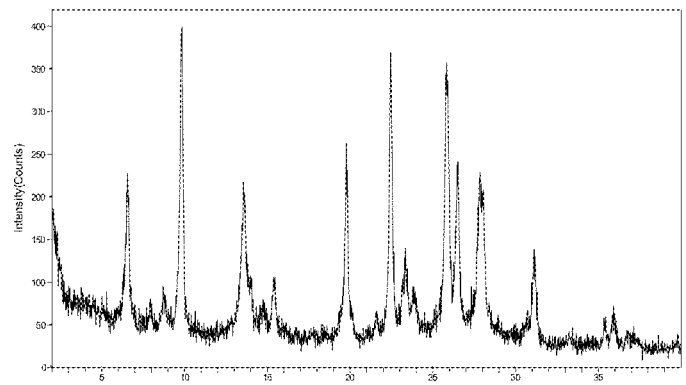
Figure 12A: XRD on Example 16
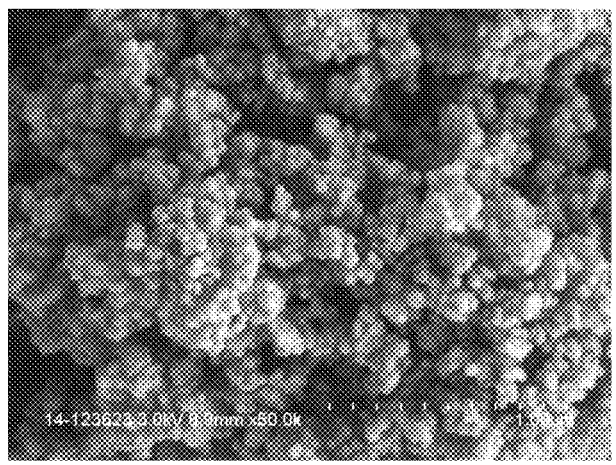
Figure 12B: SEM on Example 16

PROCESS FOR PREPARING A MOLECULAR SIEVE

CROSS REFERENCE TO RELATED APPLICATIONS

This application claims the benefit of and priority to U.S. Ser. No. 62/111,730, filed Feb. 4, 2015, and priority to European Application No. 15160258.8, filed Mar. 23, 2015, the disclosures of which are incorporated herein in their entireties.

FIELD OF THE INVENTION

The present invention relates to a mordenite molecular sieve having a small crystal size and to a process of making that mordenite molecular sieve.

BACKGROUND

Molecular sieve materials, both natural and synthetic, have been demonstrated in the past to be useful as adsorbents and to have catalytic properties for various types of hydrocarbon conversion reactions. Certain molecular sieves, such as zeolites, AlPOs, and mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes. The zeolite pores may be in the micro- (<2 nm), meso- (2 to 50 nm) or macro (>50 nm to 200 nm) size range.

Such molecular sieves, both natural and synthetic, include a wide variety of crystalline silicates. These silicates can be described as rigid three-dimensional frameworks of $SiO_4$ tetrahedra (which have four oxygen atoms at the apexes with the silicon atom being at the center) and Periodic Table Group 13 element oxide (e.g., $AlO_4$, $BO_4$) tetrahedral (which have four oxygen atoms at the apexes with the Periodic Table Group 13 element being at the center). These tetrahedra are regularly and three dimensionally cross-linked by the sharing of oxygen atoms. This arrangement provides a three-dimensional network structure defining pores that differ in size and shape, depending on the arrangement of tetrahedral and composition of the structure. The electrovalence of the tetrahedra containing the Group 13 element (e.g., aluminum or boron) is balanced by the inclusion in the crystal of a cation, for example a proton, an alkali metal or an alkaline earth metal cation. This can be expressed wherein the ratio of the Group 13 element (e.g., aluminum or boron) to the number of various cations, such as $H^+$, $Ca^{2+}/2$, $Sr^{2+}/2$, $Na^+$, $K^+$, or $Li^+$, is equal to unity. It is the presence of framework aluminum in aluminosilicates which is important in providing, for instance, the catalytic properties of these materials.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference.

Synthesis of molecular sieve materials typically involves the preparation of a synthesis mixture which comprises sources of all the elements present in the molecular sieve often with a source of hydroxide ion to adjust the pH. In many cases a structure directing agent is also present. Structure directing agents are compounds which are believed to promote the formation of molecular sieves and which are thought to act as templates around which certain molecular sieve structures can form and which thereby promote the formation of the desired molecular sieve. Various compounds have been used as structure directing agents including various types of quaternary ammonium cations.

The synthesis of molecular sieves is a complicated process. There are a number of variables that need to be controlled in order to optimise the synthesis in terms of purity, yield and quality of the molecular sieve produced. A particularly important variable is the choice of synthesis template (structure directing agent), which usually determines which framework type is obtained from the synthesis. Quaternary ammonium ions are typically used as the structure directing agents in the preparation of zeolite catalysts.

The "as-synthesised" molecular sieve will contain the structure directing agent in its pores, and is usually subjected to a calcination step to burn out the structure directing agent and free up the pores. For many catalytic applications, it is desired to convert the molecular sieve to the hydrogen form (H-form). That may be accomplished by firstly removing the structure directing agent by calcination in air or nitrogen, then ion exchanging to replace alkali metal cations (typically sodium cations) by ammonium cations, and then subjecting the molecular sieve to a final calcination to convert the ammonium form to the H-form. The H-form may then be subjected to various 'post-treatments" such as steaming and/or acid treatments to remove aluminum or other metal ions from the framework. The products of such treatments are often referred to as "post-treated".

Mordenite, a member of the large-pore zeolite family, consists of 12-membered ring pore channels interconnected by 8-membered ring pores. However, the 8-membered ring pores are too small for most molecules to enter, and so mordenite is generally considered a one-dimensional pore system. Despite this feature, mordenite is widely used in industry, particularly for alkylation, transalkylation, and (hydro) isomerization reactions. To improve physical transport in the 1-D channels, mordenite crystals are typically subjected to dealumination post-treatment. Post-treated mordenite catalysts have been used for transalkylation of heavy aromatics and have shown very encouraging performance. Mordenite is commercially available from, for example, Tosoh and Zeolyst. There is a desire to provide improved mordenite catalysts having improved catalytic performance.

SUMMARY OF THE INVENTION

The invention provides in a first aspect a mordenite zeolite comprising a structure directing agent (SDA) selected from the group consisting of TEA, MTEA and mixtures thereof within its pores, having a mesopore surface area of greater than 30 $m^2/g$ and comprising agglomerates composed of primary crystallites, wherein the primary crystallites have an average primary crystal size as measured by Transmission Election Microscopy (TEM) of less than 80 nm.

The present inventors have found that it is possible to prepare mordenite having a very small crystal size and having a high mesopore surface area. The very small primary crystal size promotes access of reactant compounds to the active sites within the pores of the mordenite, thereby increasing catalytic efficiency. The aspect ratio of the primary crystals, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM, is relatively low, for example, less than 2.0. Typically, the primary crystals are not elongated crystals having an aspect ratio greater than 2.0, or platelets.

The term "primary crystal" as used herein denotes a single, indivisible crystal in contrast to an agglomerate. Primary crystals typically adhere together through weak physical interactions (rather than chemical bonds) to form agglomerates. The words "crystal" and "crystallite" are used herein interchangeably.

References herein to the mordenite zeolite of the invention should be understood to refer to the mordenite zeolite of any aspect of the invention, or as made by any method according to the invention.

References herein to primary crystal size as measured by TEM should be understood to mean measurement of primary crystal size using the method described below in the Experimental section.

The mordenite zeolite of the first aspect of the invention comprises a structure directing agent within its pores and may also be referred to as an "as-synthesised" mordenite zeolite.

Conventionally, in order to convert "as synthesized" mordenite to the H-form, the "as-synthesized" mordenite is first calcined in air or nitrogen to remove the structure directing agent from the pores. The calcined mordenite is then ion-exchanged to replace the alkali metal cations such as sodium cation with ammonium cations. A further calcining step converts the ammonium form to the H-form.

For the mordenite zeolite of the present invention, the structure directing agent may be removed from the mordenite framework, for example, by calcining in air or an inert atmosphere such as nitrogen, prior to ion exchange. However, the inventors have also found, surprisingly, that it is in some cases possible to remove the alkali metal cations, $M^+$ from the mordenite zeolite of the present invention by ion exchange, without calcining prior to the ion exchange. In some cases the mordenite of the present invention may optionally therefore be ion-exchanged to remove the alkali metal cations without the need for pre-calcining. The ion exchanged mordenite is then converted into the H-form by calcining, which simultaneously removes the structure directing agent and converts the mordenite to the H-form.

The mordenite of the invention may then also be subjected to various forms of post-treatment. In particular, the mordenite zeolite may be treated with steam and/or acid in order to increase the mesopore surface area and/or remove aluminum from the framework, thereby increasing the ratio of silicon to alumina.

In a second aspect, the invention provides a calcined mordenite zeolite prepared by subjecting the mordenite zeolite of the first aspect of the invention to a calcining step to remove the TEA or MTEA from the pores, the calcined zeolite having a mesopore surface area of greater than 30 $m^2/g$ and comprising agglomerates composed of primary crystallites, wherein the primary crystallites have an average primary crystal size as measured by TEM of less than 80 nm.

In a third aspect, the invention provides a process for the preparation of a mordenite zeolite according to the first aspect of the invention comprising:

a) providing a synthesis mixture comprising a silicon source, an aluminum source, an alkali metal (M) hydroxide, a source of a structure directing agent (SDA) selected from the group consisting of tetraethylammonium cation (TEA), methyltriethylammonium cation (MTEA) and mixtures thereof, optional seed crystals and water, said synthesis mixture having a composition including the following molar ratios:

Si:Al$_2$ 15-40
OH$^-$:Si≤0.32
M$^+$:Si≤0.32
SDA:Si≤0.10
H$_2$O:Si<20 b) subjecting said synthesis mixture to crystallization conditions to form crystals of a mordenite zeolite comprising the structure directing agent (SDA) within its pores.

In a fourth aspect, the invention provides a process for the preparation of a calcined mordenite zeolite which comprises the steps of i) subjecting the mordenite zeolite of the first aspect of the invention to an ion exchange treatment to remove alkali metal cation $M^+$; and then ii) calcining. Optionally, the alkali metal cation, $M^+$, is removed from the mordenite by ion exchange, without calcining before the ion exchange. Alternatively, the process may include a calcination step prior to the ion exchange step.

The calcined mordenite may also be subjected to further steps after the structure directing agent has been removed, such as at least one of a further calcination step, a steam treatment step or a de-alumination step. Such further treatment steps are often referred to as "post treatment" steps.

In a fifth aspect, the invention provides the use of a mordenite zeolite according to the first or second aspect of the invention, or as prepared according to the third or fourth aspects of the invention, as a sorbent or catalyst.

In a sixth aspect, the invention provides a process for converting a feedstock comprising an organic compound to a conversion product which comprises the step of contacting said feedstock at organic compound conversion conditions with a catalyst comprising a mordenite zeolite according to the first or second aspect of the invention or as made according to the process of the third or fourth aspects of the invention. In a preferred embodiment, the process is a transalkylation process, such as the transalkylation of $C_9^+$ aromatics.

BRIEF DESCRIPTION OF THE DRAWINGS

FIGS. 1A and 1B show an XRD and a SEM, respectively, of the mordenite of Example 1.

FIGS. 2A and 2B show an XRD and a SEM, respectively, of the mordenite of Example 3.

FIGS. 3A and 3B show an XRD and a SEM, respectively, of the mordenite of Example 4.

FIGS. 4A and 4B show an XRD and a SEM, respectively, of the mordenite of Example 5.

FIGS. 5A, 5B and 5C show an XRD, a SEM and a TEM, respectively, of the mordenite of Example 6.

FIGS. 6A, 6B and 6C show an XRD, a SEM and a TEM, respectively, of the mordenite of Example 7.

FIGS. 7A and 7B show an XRD and a SEM, respectively, of the mordenite of Example 10.

FIGS. 8A, 8B and 8C show an XRD, a SEM and a TEM, respectively, of the mordenite of Example 12.

FIGS. 9A, and 9B show an XRD and a SEM, respectively, of the mordenite of Example 14.

FIG. 10 shows the primary crystal size distributions as measured by TEM of the mordenites of Example 6 (diamonds), Example 7 (squares) and Example 12 (triangles).

FIGS. 11A and 11B show an XRD and a SEM, respectively, of the mordenite of Example 15.

FIGS. 12A and 12B show an XRD and a SEM, respectively, of the mordenite of Example 16.

DETAILED DESCRIPTION OF THE INVENTION

The present inventors have found that it is possible to prepare mordenite zeolite having a very small crystal size and having a high mesopore surface area, in particular by the selection of the synthesis mixture composition.

The structure directing agent is selected from the group consisting of TEA, MTEA and mixtures thereof. As used herein, "TEA" refers to the tetraethyl ammonium cation and "MTEA" refers to the methyl triethyl ammonium cation. Those cations are known for use as structure directing agents in the synthesis of mordenite. Preferably, the structure directing agent is TEA.

The ratio $Si:Al_2$ of the mordenite zeolite according to the first and second aspects of the invention is preferably greater than 10 and may be in the range of, for example, from 10 to 60, preferably from 15 to 40. The ratio $Si:Al_2$ of the post-treated mordenite zeolite of the second aspect of the invention is preferably in the range of from 40 to 300, more preferably from 60 to 150.

The mordenite zeolite of the first and second aspects of the invention comprises agglomerates, typically irregular agglomerates. The agglomerates are composed of primary crystallites which have an average primary crystal size as measured by TEM of less than 80 nm, preferably less than 70 nm and more preferably less than 60 nm, for example, less than 50 nm. The primary crystallites may have an average primary crystal size as measured by TEM of, for example, greater than 20 nm, optionally greater than 30 nm.

Optionally, the primary crystals of the mordenite of the first and second aspects of the invention have an average primary crystal size of less than 80 nm, preferably less than 70 nm, and in some cases less than 60 nm, in each of the a, b and c crystal vectors as measured by X-ray diffraction. The primary crystallites may optionally have an average primary crystal size of greater than 20 nm, optionally greater than 30 nm, in each of the a, b and c crystal vectors, as measured by X-ray diffraction.

The mordenite zeolite of the first and second aspects of the invention will generally comprise a mixture of agglomerates of the primary crystals together with some unagglomerated primary crystals. The majority of the mordenite zeolite, for example, greater than 80 weight % or greater than 90 weight % will be present as agglomerates of primary crystals. The agglomerates are typically of irregular form. For more information on agglomerates please see Walter, D. (2013) Primary Particles—Agglomerates—Aggregates, in Nanomaterials (ed Deutsche Forschungsgemeinschaft (DFG)), Wiley-VCH Verlag GmbH & Co. KGaA, Weinheim, Germany. doi: 10.1002/9783527673919, pages 1-24. Usefully, the mordenite is not an aggregate.

Optionally, the mordenite zeolite of the first and second aspects of the invention comprises at least 50% by weight, preferably at least 70% by weight, advantageously at least 80% by weight, more preferably at least 90% by weight and optionally substantially consists of said irregular agglomerates composed of primary crystallites having a primary crystal size of less than 80 nm, preferably less than 70 nm, and more preferably less than 60 nm, for example, less than 50 nm. Preferably, the mordenite zeolite of the invention comprises less than 10% by weight of primary crystallites having a size of more than 80 nm as assessed by TEM. Preferably, the mordenite zeolite of the invention is composed of said irregular agglomerates composed of crystallites having a crystal size as measured by TEM of less than 80 nm. Preferably, the mordenite zeolite of the invention is substantially free, for example, contains less than 10% by number as assessed by TEM, of needle or platelet crystals.

Preferably, said primary crystallites of the mordenite zeolite of the first and second aspects of the invention have an aspect ratio of less than 3.0, more preferably less than 2.0, wherein the aspect ratio is defined as the longest dimension of the crystallite divided by the width of the crystallite, where the width of the crystallite is defined as the dimension of the crystallite in the middle of that longest dimension in a direction orthogonal to that longest dimension, as measured by TEM.

Said agglomerates of said primary crystallites are typically of irregular form and may be referred to as being "secondary" particles because they are formed of agglomerates of the crystallites, which are the "primary" particles.

The primary crystallites may have a narrow particle size distribution such that at least 90% of the primary crystallites by number have a primary crystal size in the range of from 20 to 80 nm, preferably in the range of from 20 to 60 nm, as measured by TEM.

The mordenite zeolite according to the first and second aspects of the invention has a mesopore surface area as measured by BET of greater than 30 $m^2/g$, preferably greater than 40 $m^2/g$, and in some cases greater than 45 $m^2/g$.

The mordenite zeolite according to the first and second aspects of the invention preferably has a total surface area of greater than 500 $m^2/g$, more preferably greater than 550 $m^2/g$, and in some cases greater than 600 $m^2/g$. The total surface area includes the surface area of the internal pores (zeolite surface area) and also the surface area on the outside of the crystals (the external surface area). The total surface area is measured by BET.

Preferably, the ratio of mesopore surface area to the total surface area for the mordenite zeolite according to the first and second aspects of the invention is greater than 0.05.

The mordenite zeolite according to the first and second aspects of the invention preferably has a mesopore volume of greater than 0.1 mL/g, more preferably greater than 0.12 mL/g, and in some cases greater than 0.15 mL/g.

The mordenite zeolite of the first aspect of the invention may be prepared by the process of the third aspect of the invention. The components of the synthesis mixture are combined and maintained under crystallisation conditions.

Suitable sources of silicon (Si) include silica, colloidal suspensions of silica, precipitated silica, alkali metal silicates such as potassium silicate and sodium silicate, tetraalkyl orthosilicates, and fumed silicas such as Aerosil and Cabosil. Preferably, the source of Si is a precipitated silica such as Ultrasil (available from Evonik Degussa) or HiSil (available from PPG Industries).

Suitable sources of aluminum (Al) include aluminum sulfate, aluminum nitrate, aluminum hydroxide, hydrated alumina such as boehmite, gibbsite and/or pseudoboehmite, sodium aluminate and mixtures thereof. Other aluminum sources include, but are not limited to, other water-soluble aluminum salts, or an aluminum alkoxide, such as aluminum isopropyloxide, or an aluminum metal, such as aluminum in the form of chips. Preferably, the aluminum source is sodium aluminate, for example an aqueous solution of sodium aluminate with a concentration in the range of 40 to 45%, or aluminum sulfate, for example an aluminum sulfate solution with a concentration in the range of from 45 to 50%.

Alternatively or in addition to previously mentioned sources of Si and Al, aluminosilicates may also be used as a source of both Si and Al.

Preferably, the Si:Al$_2$ ratio in the synthesis mixture is in the range of from 15 to 40, more preferably from 20 to 30.

The synthesis mixture also contains a source of alkali metal cation M$^+$. The alkali metal cation M$^+$ is preferably selected from the group consisting of sodium, potassium and mixtures of sodium and potassium cations. Sodium cation is preferred. Suitable sodium sources may be, for example, a sodium salt such as NaCl, NaBr or NaNO$_3$, sodium hydroxide or sodium aluminate, preferably sodium hydroxide or sodium aluminate. Suitable potassium sources may be, for example, potassium hydroxide or potassium halide such as KCl or KBr, or potassium nitrate. Preferably, the ratio M$^+$:Si in the synthesis mixture is in the range of from 0.15 to 0.32, more preferably from 0.20 to 0.32. Optionally, the ratio M$^+$:Si is less than 0.30.

The synthesis mixture also contains a source of hydroxide ions, for example, an alkali metal hydroxide such as sodium hydroxide or potassium hydroxide. Hydroxide can also be present as a counter ion of the structure directing agent or by the use of aluminum hydroxide as a source of Al. Preferably the range OH$^-$:Si is greater than 0.13, and may, for example, be in the range of from 0.15 to 0.32, preferably from 0.20 to 0.32. Optionally, the OH$^-$:Si ratio is less than 0.30.

The synthesis mixture optionally comprises seeds. The seeds may be any suitable zeolite seed crystals, such as ZSM-5, ZSM-11 or mordenite seed crystals. Preferably, the seeds are mesoporous mordenite crystals. The seeds may, for example, be present in an amount from about 0 to 20 wt %, in particular from about 0 to 10 wt %, preferably from about 0.01 to 10 wt % such as from about 0.1 wt % to about 5.0 wt % of the synthesis mixture. In a preferred embodiment, the synthesis mixture comprises seeds.

The structure directing agent, TEA and/or MTEA, preferably TEA, may be present in any suitable form, for example as a halide, but is preferably present in its hydroxide form. Suitable sources of the structure directing agent include TEABr, TEAOH, MTEACl and MTEAOH. A preferred source of structure directing agent is TEABr. Preferably, the ratio SDA:Si is in the range of from 0.005 to 0.10, more preferably from 0.02 to 0.10, especially from 0.02 to 0.05.

The present inventors have found that the synthesis of small crystal mordenite is favoured by having a relatively high solids content in the synthesis mixture. Preferably, the H$_2$O:Si ratio is no more than 20, for example, in the range of from 5 to 20, preferably from 5 to 17, especially from 10 to 17.

In the third aspect of the invention, the synthesis mixture may for example have a composition, expressed in terms of mole ratios, as indicated in the following Table:

| Mole ratio | Preferred | More preferred | Especially preferred |
|---|---|---|---|
| Si:Al$_2$ | 15 to 40 | 20 to 35 | 20 to 30 |
| OH$^-$:Si | 0.15 to 0.32 | 0.20 to 0.32 | 0.20 to <0.30 |
| M$^+$:Si | 0.15 to 0.32 | 0.20 to 0.32 | 0.20 to <0.30 |
| SDA:Si | 0.005 to 0.10 | 0.02 to 0.10 | 0.02 to 0.05 |
| H$_2$O:Si | 5 to 20 | 5 to 17 | 10 to 17 |

Crystallization can be carried out under either static or stirred conditions in a suitable reactor vessel, such as for example, polypropylene jars or Teflon® lined or stainless steel autoclaves. Suitable crystallization conditions include a temperature of about 100° C. to about 200° C., such as about 135° C. to about 160° C. Preferably, the temperature is less than 145° C. The synthesis mixture may be held at the elevated temperature for a time sufficient for crystallization to occur at the temperature used, e.g., from about 1 day to about 100 days, optionally from 1 to 50 days for example about 2 days to about 40 days. The synthesis mixture may in some cases be maintained at a first temperature for a first period of from 1 hour to 10 days and then raised to a second, higher temperature for a period of from 1 hour to 40 days. After the crystallisation step, the synthesized crystals are separated from the liquid and recovered.

In its as-synthesized form, the mordenite zeolite of the first aspect of the invention typically has a chemical composition having the following molar relationship:

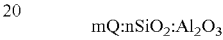

mQ:nSiO$_2$:Al$_2$O$_3$ wherein
0.001≤m/n≤0.1, for example 0.001≤m/n≤0.05,
n is at least 10, for instance from 10 to 60, preferably from 15 to 40, and
Q is the structure directing agent.

Since the as-synthesized mordenite zeolite of the first aspect of the invention contains the structure directing agent within its pore structure, the product is usually activated before use in such a manner that the organic part of the structure directing agent, i.e. TEA and/or MTEA, is at least partially removed from the zeolite.

The calcined mordenite zeolite of the second aspect of the invention is optionally prepared by calcining the mordenite zeolite of the first aspect of the invention to remove the structure directing agent. The mordenite may also be subjected to an ion-exchange step to replace the alkali or alkaline earth metal ions present in the as-synthesized product with other cations. Preferred replacing cations include metal ions, hydrogen ions, hydrogen precursor such as ammonium ions and mixtures thereof, more preferably hydrogen ions or hydrogen precursors. For instance the mordenite zeolite of the first aspect of the invention may be subjected to an ion-exchange step to replace the alkali or alkaline earth metal ions with ammonium cations, followed by calcination to convert the zeolite in ammonium form to a zeolite in hydrogen form. In one embodiment, the mordenite zeolite of the first aspect of the invention is first subjected to a calcination step, sometimes referred to as a "pre-calcination" to remove the structure directing agent from the pores of the mordenite, followed by an ion-exchange treatment, followed by a further calcination step. However, the present inventors have found that for the mordenite zeolite of the present invention, a pre-calcination step is not always required. In an alternative embodiment, the mordenite zeolite of the first aspect of the invention is thus subjected to an ion-exchange treatment without being subjected to a prior calcination step (or pre-calcination), and, following the ion exchange treatment, is calcined to remove the structure directing agent from the pores, thereby providing the calcined mordenite zeolite of the second aspect of the invention.

The ion-exchange step may involve, for example, contacting the mordenite zeolite with an aqueous ion exchange solution. Such contact may be take place, for example, from 1 to 5 times. The contacting with the ion exchange solution is optionally at ambient temperature, or alternatively may be at an elevated temperature. For example, the zeolite of the first aspect of the invention may be ion exchanged by contact with aqueous ammonium nitrate solution at room temperature followed by drying and calcination.

Suitable calcination conditions include heating at a temperature of at least about 300° C., preferably at least about 370° C. for at least 1 minute and generally not longer than 20 hours, for example, for a period of from 1 hour to 12 hours. While subatmospheric pressure can be employed for the thermal treatment, atmospheric pressure is desired for reasons of convenience. The thermal treatment can be performed at a temperature up to about 925° C. For instance, the thermal treatment can be conducted at a temperature of from 400 to 600° C., for instance from 500 to 550° C., in the presence of an oxygen-containing gas.

The calcined mordenite zeolite of the second aspect of the invention typically has a chemical composition having the following molar relationship:

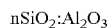

$$nSiO_2 : Al_2O_3$$

wherein n is at least 10, for example 10 to 60, more particularly 15 to 40.

The calcined mordenite zeolite of the second aspect of the invention may be used as is as a catalyst or as a sorbent without further treatment or it may be subjected to post-treatments such as steaming and/or acid washing.

Optionally, the calcined zeolite of the second aspect of the invention is subjected to steam treatment at a temperature of at least 200° C., preferably at least 350° C., more preferably at least 400° C., in some cases at least 500° C., for a period of from 1 to 20 hours, preferably from 2 to 10 hours. Optionally, the steamed zeolite is then subjected to treatment with an aqueous solution of an acid, preferably an organic acid, such as a carboxylic acid. Oxalic acid is a preferred acid. Optionally, the steamed zeolite is treated with an aqueous solution of an acid at a temperature of at least 50° C., preferably at least 60° C., for a period of at least 1 hour, preferably at least 4 hours, for example, in the range of from 5 to 20 hours.

Preferably, the post-treated mordenite zeolite has a chemical composition having the following molar relationship:

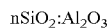

$$nSiO_2 : Al_2O_3$$

wherein n is at least 50, more preferably at least 70, and in some cases at least 100.

The mordenite zeolite of the invention can be used directly as a catalyst, or alternatively can be compounded with one or more other components such as binder. The mordenite zeolite may be used as an adsorbent or as a catalyst to catalyze a wide variety of organic compound conversion processes including many of present commercial/industrial importance. The conversion of hydrocarbon feeds can take place in any convenient mode, for example in fluidized bed, moving bed, or fixed bed reactors depending on the types of process desired.

The mordenite zeolite of the present invention, when employed either as an adsorbent or as a catalyst in an organic compound conversion process should be dehydrated, at least partially. This can be done by heating to a temperature in the range of about 100° C. to about 500° C., such as about 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the mordenite in a vacuum, but a longer time is required to obtain a sufficient amount of dehydration.

The mordenite zeolite of the present invention can be formulated into a catalyst composition by combination with other materials, such as hydrogenating components, binders and/or matrix materials that provide additional hardness or catalytic activity to the finished catalyst. These other materials can be inert or catalytically active materials.

The mordenite zeolite described herein may be intimately combined with a hydrogenating component, such as tungsten, vanadium, molybdenum, rhenium, nickel, cobalt, chromium, manganese, or a noble metal such as platinum or palladium where a hydrogenation-dehydrogenation function is to be performed. Such component can be incorporated in the composition by way of cocrystallization, exchanged into the composition to the extent a Group IIIA element, e.g., aluminum, is in the structure, impregnated therein or intimately physically admixed therewith. Such component can be impregnated in or onto the mordenite zeolite such as, for example, by, in the case of platinum, treating the mordenite zeolite with a solution containing a platinum metal-containing ion. Thus, suitable platinum compounds for this purpose include chloroplatinic acid, platinous chloride and various compounds containing the platinum amine complex. Combinations of metals and methods for their introduction can also be used.

As in the case of many catalysts, it may be desirable to incorporate the mordenite zeolite of the present invention with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the mordenite, i.e., combined therewith or present during synthesis of the mordenite, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., montmorillonite, bentonite, subbentonite and kaolin such as the kaolins commonly known as Dixie, McNamee, Georgia and Florida clays or others in which the main mineral constituent is halloysite, kaolinite, nacrite or anauxite, to improve the crush strength of the catalyst under commercial operating conditions. Such clays can be used in the raw state as originally mined or after being subjected to calcination, acid treatment or chemical modification. These binder materials are resistant to the temperatures and other conditions, e.g. mechanical attrition, which occur in various hydrocarbon conversion processes. Thus the mordenite zeolite of the present invention or manufactured by the process of the present invention may be used in the form of an extrudate with a binder. They are typically bound by forming a pill, sphere, or extrudate. The extrudate is usually formed by extruding the molecular sieve, optionally in the presence of a binder, and drying and calcining the resulting extrudate.

Use of a material in conjunction with the mordenite zeolite of the present invention or manufactured by the process of the present invention, i.e. combined therewith or present during synthesis of zeolite, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions.

In addition to the foregoing materials, the mordenite of the present invention can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of mordenite zeolite and inorganic oxide matrix may vary widely, with the mordenite content ranging from about 1 to about 90 percent by weight and more usually, particularly when the composite is prepared in the form of beads or extrudates, in the range of about 2 to about 80 weight percent of the composite.

EXAMPLES

The following examples illustrate the present invention. Numerous modifications and variations are possible and it is to be understood that within the scope of the appended claims, the invention may be practiced otherwise than as specifically described herein.

Experimental

Measurement of Average Primary Particle Size and Primary Particle Size Distribution.

The measurement of average primary particle size and primary particle size distribution was carried out as follows. Several TEM photographs of the zeolite sample were taken, primary particles were identified and measured. For each primary particle having an aspect ratio greater than 1, the longest dimension was identified by drawing a line between the two points at the edge of the particle which were the furthest apart. Then the length of the primary particle along a 45° diagonal to that longest dimension and passing through the mid-point of that longest dimension was measured as the particle size. Each measurement was grouped by being assigned to one of about 10 particle size ranges covering the range of sizes found in the sample. More than 300 primary particles were measured and then the numbers in each particle size range were plotted to show the particle size distribution, as shown in FIG. 10. For example, size ranges centred around 187.5, 250, 312.5, 375, 437.5, 500, 562.5 and 625 Angstroms could be used. The percent (%) crystals value on the y-axis was calculated from: Number of particles in each group/total number of particles measured multiplied by 100. The average particle size was calculated as the arithmetical mean based on the grouped results.

Measurement of Total Surface Area and Mesopore Surface Area by BET.

The total BET and the t-Plot micropore surface area were measured by nitrogen adsorption/desorption with a Micromeritics Tristar II 3020 instrument after degassing of the calcined zeolite powders for 4 hrs at 350° C. The mesopore surface area was obtained by the subtraction of the t-plot micropore from the total BET surface area. The mesopore volume was derived from the same data set. More information regarding the method can be found, for example, in "*Characterization of Porous Solids and Powders: Surface Area, Pore Size and Density*", S. Lowell et al., Springer, 2004.

X-ray Diffraction Patterns.

The X-ray diffraction data (powder XRD or XRD) were collected with a Bruker D4 Endeavor diffraction system with a VANTEC multichannel detector using copper K-alpha radiation. The diffraction data were recorded by scanning mode with 0.018 degrees two-theta, where theta is the Bragg angle, and using an effective counting time of about 30 seconds for each step.

Measurement of the Crystal Sizes in the a, b and c Vectors.

The crystal sizes in the a, b and c crystal vectors were calculated based on the three (200), (020) and (002) peaks in the X-ray diffraction patterns using the Scherrer equation (P. Scherrer, N. G. W. Gottingen, *Math-Pys.*, 2, p. 96-100 (1918)). The method and its application to zeolites is also described in A. W. Burton, K. Ong, T. Rea, I. Y. Chan, *Microporous and Mesoporous Materials*, 117, p. 75-90 (2009). For the measurements described herein the Jade version 9.5.1 X-ray diffraction analysis software by Materials Data, Inc., was used to perform the calculation.

Alpha Value

The alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. The experimental conditions of the test used herein included a constant temperature of 538° C. and a variable flow rate as described in detail in the Journal of Catalysis, Vol. 61, p. 395 (1980).

Comparative Example 1

TEABr with NaOH/Si Ratio of 0.40

A mixture was prepared from 1,030 g of water, 67 g of TEABr (50% solution), 212 g of Ultrasil silica, 48.7 g of sodium aluminate solution (45%), and 80 g of 50% sodium hydroxide solution. Then 10 g of Mordenite seeds was added to the mixture. The mixture had the following molar composition:

$SiO_2/Al_2O_3$—26.08
$H_2O/SiO_2$—19.78
$OH^-/SiO_2$—0.402
$Na^+/SiO_2$—0.402
$TEA/SiO_2$—0.049

The mixture was reacted at 300° F. (150° C.) in a 5-gal autoclave with stirring at 250 RPM for 72 hours. The product was filtered, washed with deionized (DI) water and dried at 250° F. (120° C.). The XRD pattern, FIG. 1A of the as-synthesized material showed the typical pure phase of Mordenite topology. The SEM, FIG. 1B, of the as-synthesized material showed morphology of mixed morphologies of large crystallites. The as-synthesized crystals were first pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~17, surface area of 612 m²/g and mesopore surface area of 13.7 m²/g, hexane sorption of 63.5 mg/g and an Alpha value of 640.

Comparative Example 2

TEABr with NaOH/Si Ratio of 0.41, No Seeds

A mixture was prepared from 1,000 g of water, 67 g of TEABr (50% solution), 212 g of Ultrasil silica, 48.7 g of sodium aluminate solution (45%), and 81 g of 50% sodium hydroxide solution. The mixture had the following molar composition:

$SiO_2/Al_2O_3$—26.08
$H_2O/SiO_2$—19.28
$OH^-/SiO_2$—0.406
$Na^+/SiO_2$—0.406
$TEA/SiO_2$—0.049

The mixture was reacted at 300° F. (150° C.) in a 2-1 autoclave with stirring at 250 RPM for 72 hours. The product was filtered, washed with deionized (DI) water and dried at 250° F. (120° C.). The XRD pattern of the as-synthesized material showed the typical pure phase of Mordenite topology. The SEM of the as-synthesized material showed mixed morphologies of various sized of crystallites. The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~16, surface area of 550 m²/g and mesopore surface area of 17 m²/g, hexane sorption of 77 mg/g and an Alpha value of 1100.

Comparative Example 3

TEABr with NaOH/Si Ratio of 0.345

A mixture was prepared from 1,030 g of water, 67 g of TEABr (50% solution), 212 g of Ultrasil silica, 48.7 g of sodium aluminate solution (45%), and 65 g of 50% sodium hydroxide solution. Then 10 g of Mordenite seeds was added to the mixture. The mixture had the following molar composition:

$SiO_2/Al_2O_3$—26.08
$H_2O/SiO_2$—19.62
$OH^-/SiO_2$—0.345
$Na^+/SiO_2$—0.345
$TEA/SiO_2$—0.049

The mixture was reacted at 300° F. (150° C.) in a 2-1 autoclave with stirring at 250 RPM for 72 hours. The product was filtered, washed with deionized (DI) water and dried at 250° F. (120° C.). The XRD pattern, FIG. 2A, of the as-synthesized material showed the typical pure phase of Mordenite topology. The SEM, FIG. 2B, of the as-synthesized material showed mixed morphologies of various sized of crystallites. The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~19, surface area of 609 m²/g and mesopore surface area of 30 m²/g, hexane sorption of 64.3 mg/g and an Alpha value of 550. The reduction in $NaOH/SiO_2$ ratio to 0.345 led to smaller crystals and an increased mesopore surface area.

Example 4

Synthesis of meso-Mordenite Crystals using TEABr as SDA with NaOH/Si of 0.29

A mixture was prepared from 1,030 g of water, 67 g of TEABr (50% solution), 212 g of Ultrasil silica, 48.7 g of sodium aluminate solution (45%), and 51 g of 50% sodium hydroxide solution. Then 10 g of Mordenite seeds was added to the mixture. The mixture had the following molar composition:

$SiO_2/Al_2O_3$—26.08
$H_2O/SiO_2$—19.48
$OH^-/SiO_2$—0.291
$Na^+/SiO_2$—0.291
$TEA/SiO_2$—0.049

The mixture was reacted at 300° F. (150° C.) in a 2-liter autoclave with stirring at 250 RPM for 72 hours. The product was filtered, washed with deionized (DI) water and dried at 250° F. (120° C.). The XRD pattern, FIG. 3A, of the as-synthesized material showed the typical pure phase of Mordenite topology. The SEM, FIG. 3B, of the as-synthesized material showed morphology of irregularly-shaped agglomerates composed of smaller & more uniform morphology of crystallites than previous examples. The primary crystallite size appeared smaller than 80 nm based on the SEM. The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of 20.1, total surface area of 618 m²/g, and mesopore surface area of 41 m²/g, mesopore volume of 0.135 mL/g, hexane sorption of 57.9 mg/g and an Alpha value of 960. The resulting mesopore surface area is much higher than those previous examples; the crystal size is also smaller and the particle size distribution is more uniform.

Post-Treatment: Steaming and Oxalic Acid Wash on H-Form Crystals

The hydrogen-form crystals were steamed at 650° C. for 4 hrs and then subjected to an oxalic acid wash for about 12 hrs at 70° C. The resulting post-treated Mordenite crystals had a $SiO_2/Al_2O_3$ molar ratio of 306/1, total surface area of 591 m²/g, a mesopore surface area of 54 m²/g, mesopore volume of 0.19 cc/g, hexane sorption of 52.9 mg/g and an Alpha value of 48. XRD on post-treated crystals showed Mordenite topology with good crystallinity.

Example 5

Synthesis of meso-Mordenite Crystals using TEABr as SDA with NaOH/Si of 0.29 at Larger Scale A mixture was prepared from 10,300 g of water, 670 g of TEABr (50% solution), 2,120 g of Ultrasil silica, 487 g of sodium aluminate solution (45%), and 510 g of 50% sodium hydroxide solution. Then 20 g of Mordenite seeds was added to the mixture. The mixture had the following molar composition:

$SiO_2/Al_2O_3$—26.08
$H_2O/SiO_2$—19.48
$OH^-/SiO_2$—0.291
$Na^+/SiO_2$—0.291
$TEA/SiO_2$—0.049

The mixture was reacted at 300° F. (150° C.) in a 5-gal autoclave with stirring at 250 RPM for 72 hours. The product was filtered, washed with deionized (DI) water and dried at 250° F. (120° C.). The XRD pattern, FIG. 4A, of the as-synthesized material showed the typical pure phase of Mordenite topology. The SEM, FIG. 4B, of the as-synthesized material showed morphology of irregularly-shaped agglomerates composed of small crystallites. The average primary crystallite size appeared smaller than 80 nm based on the SEM. The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~21, surface area of 624 m$^2$/g and mesopore surface area of 44 m$^2$/g, hexane sorption of 61.8 mg/g and an Alpha value of 780.

Example 6

Synthesis of meso-Mordenite Crystals using TEABr as SDA at Higher Solids and a Lower Reaction Temperature A mixture was prepared from 9,300 g of water, 804 g of TEABr (50% solution), 2,544 g of Ultrasil silica, 584 g of sodium aluminate solution (45%), and 612 g of 50% sodium hydroxide solution. Then 30 g of Mordenite seeds was added to the mixture. The mixture had the following molar composition:
$SiO_2/Al_2O_3$—26.10
$H_2O/SiO_2$—15.11
$OH^-/SiO_2$—0.291
$Na^+/SiO_2$—0.291
$TEA/SiO_2$—0.049

The mixture was reacted at 290° F. (145° C.) in a 5-gal autoclave with stirring at 350 RPM for 72 hours. The product was filtered, washed with deionized (DI) water and dried at 250° F. (120° C.). The XRD pattern, FIG. 5A, of the as-synthesized material showed the typical pure phase of Mordenite topology. The SEM (FIG. 5B) & TEM (FIG. 5C) of the as-synthesized material showed morphology of irregularly-shaped agglomerates composed of small crystallites. Several TEM photos on this example were taken and used to measure primary particle size and particle size distribution as described above and the results are shown in FIG. 10.

The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~21, surface area of 637 m$^2$/g and mesopore surface area of 56 m$^2$/g, Hexane sorption of 53.3 mg/g and an Alpha value of 1200.

Example 7

Synthesis of meso-Mordenite Crystals using TEABr as SDA and carried out as a 2-Step Reaction A mixture was prepared from 9,300 g of water, 804 g of TEABr (50% solution), 2,544 g of Ultrasil silica, 584 g of sodium aluminate solution (45%), and 612 g of 50% sodium hydroxide solution. Then 30 g of Mordenite seeds was added to the mixture. The mixture had the following molar composition:
$SiO_2/Al_2O_3$—26.10
$H_2O/SiO_2$—15.11
$OH^-/SiO_2$—0.291
$Na^+/SiO_2$—0.291
$TEA/SiO_2$—0.049

The mixture was reacted at 250° F. (120° C.) for 36 hrs and then increase to 290° F. (143° C.) for another 36 hrs in a 5-gal autoclave with stirring at 350 RPM. The product was filtered, washed with deionized (DI) water and dried at 250° F. (120° C.). The XRD pattern, FIG. 6A, of the as-synthesized material showed the typical pure phase of Mordenite topology. The SEM (FIG. 6B) and TEM (FIG. 6C), of the as-synthesized material showed morphology of irregularly-shaped agglomerates composed of small crystallites. Several TEM photos on this example were taken and used to measure primary particle size and particle size distribution as described above, and the results are shown in FIG. 10. The average primary crystal size with a, b and c crystal vectors as measured by X-ray diffraction were 55 nm (200 peak), 54 nm (020 peak) and 40 nm (002 peak).

The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~21.6, surface area of 639 m$^2$/g and mesopore surface area of 58.5 m$^2$/g, hexane sorption of 54.9 mg/g and an Alpha value of 900. The two step temperature profile resulted in smaller crystals.

Example 8

Synthesis of meso-Mordenite Crystals using TEABr as SDA; Another Example carried out as a 2-Step Reaction A mixture was prepared from 9,300 g of water, 804 g of TEABr (50% solution), 2,544 g of Ultrasil silica, 584 g of sodium aluminate solution (45%), and 612 g of 50% sodium hydroxide solution. Then 30 g of Mordenite seeds was added to the mixture. The mixture had the following molar composition:
$SiO_2/Al_2O_3$—26.10
$H_2O/SiO_2$—15.11
$OH^-/SiO_2$—0.291
$Na^+/SiO_2$—0.291
$TEA/SiO_2$—0.049

The mixture was reacted at 240° F. (115° C.) for 48 hrs and then the temperature was increased to 280° F. (138° C.) for another 48 hrs in a 5-gal autoclave with stirring at 350 RPM for 72 hours. The product was filtered, washed with deionized (DI) water and dried at 250° F. (120° C.). The XRD pattern of the as-synthesized material showed the typical pure phase of Mordenite topology. The SEM of the as-synthesized material showed morphology of irregularly-shaped agglomerates composed of small crystallites. The average primary crystallite size appeared smaller than 80 nm based on the SEM.

The as-synthesized crystals were converted into the hydrogen form by three ion exchanges with ammonium nitrate solution at room temperature and 60° C. without pre-calcination at high temperature, followed by drying at 250° F. (120° C.) and calcination at 1000° F. (540° C.) for 6 hours. The resulting Mordenite crystals had a $SiO_2/Al_2O_3$ molar ratio of ~20.5, surface area of 574 m$^2$/g and mesopore surface area of 61 m$^2$/g, hexane sorption of 59.3 mg/g and an Alpha value of 780 for the exchanged sample at room temperature and a surface area of 621 m$^2$/g and mesopore surface area of 62 m$^2$/g, hexane sorption of 68 mg/g and an Alpha value of 1300 at 60° C. This Example showed that small meso-Mordenite crystals could be ion-exchanged without a pre-calcination at high temperature to remove or decompose the SDA.

Example 9

Synthesis of meso-Mordenite Crystals using TEABr as SDA at Higher TEA/Si Ratio of 0.1

A mixture was prepared from 9,300 g of water, 1,608 g of TEABr (50% solution), 2,544 g of Ultrasil silica, 584 g of sodium aluminate solution (45%), and 612 g of 50% sodium hydroxide solution. Then 30 g of Mordenite seeds was added to the mixture. The mixture had the following molar composition:

$SiO_2/Al_2O_3$—26.10
$H_2O/SiO_2$—15.69
$OH^-/SiO_2$—0.291
$Na^+/SiO_2$—0.291
$TEA/SiO_2$—0.098

The mixture was reacted at 290° F. (150° C.) in a 5-gal autoclave with stirring at 350 RPM for 72 hours. The product was filtered, washed with deionized (DI) water and dried at 250° F. (120° C.). The XRD pattern of the as-synthesized material showed the typical pure phase of Mordenite topology. The SEM of the as-synthesized material showed morphology of irregularly-shaped agglomerates composed of small crystallites. The average primary crystallite size appeared smaller than 80 nm based on the SEM. The as-synthesized crystals were pre-calcined in nitrogen at 1000° F. and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~21.4, surface area of 610 m$^2$/g and mesopore surface area of 44 m$^2$/g, hexane sorption of 58.6 mg/g and an Alpha value of 1300.

Example 10

Synthesis of meso-Mordenite Crystals using TEABr as SDA at Lower TEA/Si Ratio of 0.03

A mixture was prepared from 9,300 g of water, 515 g of TEABr (50% solution), 2,798 g of Ultrasil silica, 702 g of sodium aluminate solution (43%), and 583 g of 50% sodium hydroxide solution. Then 30 g of Mordenite seeds was added to the mixture. The mixture had the following molar composition:

$SiO_2/Al_2O_3$—23.93
$H_2O/SiO_2$—13.64
$OH^-/SiO_2$—0.273
$Na^+/SiO_2$—0.273
$TEA/SiO_2$—0.029

The mixture was reacted at 290° F. (150° C.) in a 5-gal autoclave with stirring at 350 RPM for 72 hours. The product was filtered, washed with deionized (DI) water and dried at 250° F. (120° C.). The XRD pattern, FIG. 7A, of the as-synthesized material showed the typical pure phase of Mordenite topology. The SEM, FIG. 7B, of the as-synthesized material showed morphology of irregularly-shaped agglomerates composed of small crystallites. The average primary crystallite size appeared smaller than 80 nm based on the SEM. The as-synthesized crystals were pre-calcined in nitrogen at 1000° F. and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~20, surface area of 609 m$^2$/g and mesopore surface area of 48.4 m$^2$/g, Hexane sorption of 52.3 mg/g and an Alpha value of 750.

Example 11

Synthesis of Mordenite Crystals using TEABr as SDA at Lower TEA/Si Ratio of 0.01

A mixture was prepared from 9,940 g of water, 189 g of TEABr (50% solution), 2,968 g of Ultrasil silica, 682 g of sodium aluminate solution (45%), and 714 g of 50% sodium hydroxide solution. Then 20 g of Mordenite seeds was added to the mixture. The mixture had the following molar composition:

$SiO_2/Al_2O_3$—26.08
$H_2O/SiO_2$—13.54
$OH^-/SiO_2$—0.291
$Na^+/SiO_2$—0.291
$TEA/SiO_2$—0.010

The mixture was reacted at 290° F. (150° C.) in a 5-gal autoclave with stirring at 350 RPM for 72 hours. The product was filtered, washed with deionized (DI) water and dried at 250° F. (120° C.). The XRD pattern of the as-synthesized material showed the typical pure phase of Mordenite topology. The SEM of the as-synthesized material showed morphology of irregularly-shaped agglomerates composed of small crystallites. The average primary crystallite size appeared smaller than 80 nm based on the SEM. More uniform crystal size and morphology were produced from the 5-gal reaction. The as-synthesized crystals were pre-calcined in nitrogen at 1000° F. and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~19.5, surface area of 530 m$^2$/g and mesopore surface area of 47 m$^2$/g, hexane sorption of 48.3 mg/g and an Alpha value of 650.

Example 12

Synthesis of Mordenite Crystals using TEABr as SDA at Lower Si:$Al_2O_3$ Ratio of 23.50

A mixture was prepared from 9,350 g of water, 820 g of TEABr (50% solution), 2,544 g of Ultrasil silica, 650 g of sodium aluminate solution (45%), and 590 g of 50% sodium hydroxide solution. Then 30 g of Mordenite seeds was added to the mixture. The mixture had the following molar composition:

$SiO_2/Al_2O_3$—23.50
$H_2O/SiO_2$—15.23
$OH^-/SiO_2$—0.294
$Na^+/SiO_2$—0.294
$TEA/SiO_2$—0.050

The mixture was reacted at 290° F. (150° C.) in a 5-gal autoclave with stirring at 250 RPM for 72 hours. The product was filtered, washed with deionized (DI) water and dried at 250° F. (120° C.). The XRD pattern, FIG. 8A, of the as-synthesized material showed the typical pure phase of Mordenite topology. The SEM (FIG. 8B) & TEM (FIG. 8C) of the as-synthesized material showed morphology of irregularly-shaped agglomerates composed of small crystallites. Several TEM photos on this example were taken and used to measure primary particle size and particle size distribution as described above, and the results are shown in FIG. 10. The average primary crystal sizes in the a, b and c crystal vectors as measured by x-ray diffraction were 44 nm (200 peak), 51 nm (020 peak) and 56 nm (002 peak).

The as-synthesized crystals were pre-calcined in nitrogen at 1000° F. and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~19, surface area of 621 m$^2$/g and mesopore surface area of 51 m$^2$/g, hexane sorption of 57 mg/g and an Alpha value of 1000.

Example 13

Synthesis of Mordenite Crystals using TEABr as SDA at Higher Si:Al$_2$O$_3$ Ratio of 33.65

A mixture was prepared from 9,300 g of water, 804 g of TEABr (50% solution), 2,544 g of Ultrasil silica, 450 g of sodium aluminate solution (45%), and 612 g of 50% sodium hydroxide solution. Then 30 g of Mordenite seeds was added to the mixture. The mixture had the following molar composition:

$SiO_2/Al_2O_3$—33.65
$H_2O/SiO_2$—15.01
$OH^-/SiO_2$—0.269
$Na^+/SiO_2$—0.269
$TEA/SiO_2$—0.049

The mixture was reacted at 290° F. (150° C.) in a 5-gal autoclave with stirring at 350 RPM for 72 hours. The product was filtered, washed with deionized (DI) water and dried at 250° F. (120° C.). The XRD pattern of the as-synthesized material showed the typical pure phase of Mordenite topology. The SEM of the as-synthesized material showed morphology of irregularly-shaped agglomerates composed of small crystallites. The average primary crystallite size appeared smaller than 80 nm based on the SEM. The as-synthesized crystals were pre-calcined in nitrogen at 1000° F. and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~27, surface area of 637 m$^2$/g and mesopore surface area of 50.5 m$^2$/g, hexane sorption of 56.7 mg/g and an Alpha value of 1200.

Example 14

Synthesis of Mordenite Crystals using Methyl Triethylammonium Chloride (MTEACl) as SDA A mixture was prepared from 9,680 g of water, 670 g of Methyl Triethylammonium Chloride (97% solution), 2,750 g of Ultrasil silica, 583 g of sodium aluminate solution (45%), and 649 g of 50% sodium hydroxide solution. Then 30 g of Mordenite seeds was added to the mixture. The mixture had the following molar composition:

$SiO_2/Al_2O_3$—26.21
$H_2O/SiO_2$—14.02
$OH^-/SiO_2$—0.280
$Na^+/SiO_2$—0.280
$MTEA/SiO_2$—0.050

The mixture was reacted at 290° F. (150° C.) in a 5-gal autoclave with stirring at 350 RPM for 72 hours. The product was filtered, washed with deionized (DI) water and dried at 250° F. (120° C.). The XRD pattern, FIG. 9A, of the as-synthesized material showed the typical pure phase of Mordenite topology. The SEM, FIG. 9B, of the as-synthesized material showed morphology of irregularly-shaped agglomerates composed of small crystallites. The average primary crystallite size appeared smaller than 80 nm based on the SEM. The as-synthesized crystals w/o the pre-calcination were converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~22.4, surface area of 640 m$^2$/g and mesopore surface area of 54 m$^2$/g, hexane sorption of 57.5 mg/g and an Alpha value of 1100. This Example showed that small meso-Mordenite crystals could be made using MTEA as structure directing agent and that those crystals could be ion-exchanged without the pre-calcination at high temperature.

Example 15

Synthesis of Mordenite Crystals using TEABr as SDA and ~1% of ZSM-5 as Seeds

A mixture was prepared from 9,300 g of water, 804 g of TEABr (50% solution), 2,544 g of Ultrasil silica, 584 g of sodium aluminate solution (45%), and 612 g of 50% sodium hydroxide solution. Then 26 g of ZSM-5 seeds (Si/Al$_2$~50/1) was added to the mixture. The mixture had the following molar composition:

$SiO_2/Al_2O_3$—26.10
$H_2O/SiO_2$—15.11
$OH^-/SiO_2$—0.291
$Na^+/SiO_2$—0.291
$MTEA/SiO_2$—0.049

The mixture was reacted at 280° F. (137.8° C.) in a 5-gal autoclave with stirring at 350 RPM for 72 hours. The product was filtered, washed with deionized (DI) water and dried at 250° F. (120° C.). The XRD pattern, FIG. 11A, of the as-synthesized material showed the typical phase of Mordenite topology. The SEM (FIG. 11B) of the as-synthesized material showed morphology of irregularly-shaped agglomerates composed of small crystallites. The average primary crystallite size appeared smaller than 80 nm based on the SEM.

The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a $SiO_2/Al_2O_3$ molar ratio of ~21.2, surface area of 602 m$^2$/g and mesopore surface area of 50 m$^2$/g, Hexane sorption of 59.4 mg/g and an Alpha value of 1300.

Example 16

Synthesis of Mordenite Crystals using TEABr as SDA and ~5% of ZSM-5 as Seeds

A mixture was prepared from 9,300 g of water, 804 g of TEABr (50% solution), 2,544 g of Ultrasil silica, 584 g of sodium aluminate solution (45%), and 612 g of 50% sodium hydroxide solution. Then 130 g of ZSM-5 seeds (Si/Al$_2$~50/1) was added to the mixture. The mixture had the following molar composition:

SiO$_2$/Al$_2$O$_3$—26.10
H$_2$O/SiO$_2$—15.0
OH$^-$/SiO$_2$—0.291
Na$^+$/SiO$_2$—0.291
MTEA/SiO$_2$—0.049

The mixture was reacted at 280° F. (137.8° C.) in a 5-gal autoclave with stirring at 350 RPM for 72 hours. The product was filtered, washed with deionized (DI) water and dried at 250° F. (120° C.). The XRD pattern, FIG. 12A, of the as-synthesized material showed the typical phase of Mordenite topology. The SEM, FIG. 12B, of the as-synthesized material showed morphology of irregularly-shaped agglomerates composed of small crystallites. The average primary crystallite size appeared smaller than 80 nm based on the SEM.

The as-synthesized crystals were pre-calcined in nitrogen at 1000° F. (540° C.) and then converted into the hydrogen form by three ion exchanges with ammonium nitrate solution at room temperature, followed by drying at 250° F. (120° C.) and calcination at 1000° F. (540° C.) for 6 hours. The resulting Mordenite crystals had a SiO$_2$/Al$_2$O$_3$ molar ratio of ~22.1, surface area of 594 m$^2$/g and mesopore surface area of 46 m$^2$/g, Hexane sorption of 63.8 mg/g and an Alpha value of 1500.

It will be appreciated that various presently unforeseen or unanticipated alternatives, modifications, variations or improvements therein may be subsequently made by those skilled in the art, and are also intended to be encompassed by the following claims.

The disclosures of the foregoing publications are hereby incorporated by reference in their entirety. The appropriate components and aspects of the foregoing publications may also be selected for the present materials and methods in embodiments thereof.

The invention claimed is:

1. A mordenite zeolite comprising a structure directing agent (SDA) selected from the group consisting of TEA, MTEA and mixtures thereof within its pores, having a mesopore surface area of greater than 30 m$^2$/g and comprising agglomerates composed of primary crystallites, wherein the primary crystallites have an average primary crystal size as measured by TEM of less than 80 nm.

2. The mordenite zeolite of claim 1, wherein the primary crystallites have an average primary crystal size of less than 80 nm in each of the a, b and c crystal vectors as measured by X-ray diffraction.

3. The mordenite zeolite of claim 1, wherein at least 90% by number of the primary crystallites have a primary crystal size of less than 80 nm as measured by TEM.

4. The mordenite zeolite of claim 1, wherein said primary crystallites have an aspect ratio of less than 2, wherein the aspect ratio is defined as the longest dimension of the crystallite divided by the width of the crystallite, where the width of the crystallite is defined as the dimension of the crystallite in the middle of that longest dimension in a dimension orthogonal to that longest dimension, as measured by TEM.

5. The mordenite zeolite of claim 1 having a mesopore surface area of greater than 40 m$^2$/g.

6. The mordenite zeolite of claim 1, wherein the ratio of mesopore surface area to the total surface area is greater than 0.05.

7. A calcined mordenite zeolite prepared by subjecting the mordenite zeolite of claim 1 to a calcining step, the calcined mordenite zeolite having a mesopore surface area of greater than 30 m$^2$/g and comprising agglomerates composed of primary crystallites, wherein the primary crystallites have an average primary crystal size as measured by TEM of less than 80 nm.

8. The calcined mordenite zeolite of claim 7, wherein the Si:Al$_2$ molar ratio is greater than or equal to 50.

9. A process for the preparation of a mordenite zeolite of claim 1 comprising:
   a) providing a synthesis mixture comprising a silicon source, an aluminum source, an alkali metal (M) hydroxide, a source of a structure directing agent (SDA) selected from the group consisting of TEA, MTEA and mixtures thereof, optionally seed crystals and water, said synthesis mixture having a composition including the following molar ratios:

Si:Al$_2$ 15-40

OH$^-$:Si≤0.32

M$^+$:Si≤0.32

SDA:Si≤0.10

H$_2$O:Si<20 b) subjecting said synthesis mixture to crystallization conditions which include heating the synthesis mixture at a temperature in the range of from 100° C. to 160° C. to form crystals of a mordenite zeolite comprising the structure directing agent (SDA) within its pores.

10. The process of claim 9 wherein the silicon source is a precipitated silica.

11. The process of claim 9, wherein the aluminum source is a sodium aluminate solution or an aluminum sulfate solution.

12. The process of claim 9, wherein the SDA source is selected from the group consisting of tetraethylammonium bromide (TEABr), tetraethylammonium hydroxide (TEAOH), methyltriethylammonium chloride (MTEACl), methyltriethylammonium hydroxide (MTEAOH), and mixtures thereof.

13. A process for the preparation of a calcined mordenite zeolite which comprises the steps of i) subjecting the mordenite zeolite of claim 1 to an ion exchange treatment to remove alkali metal cation M$^+$, and then ii) calcining the mordenite zeolite at a temperature of equal to or greater than 500° C. for a period of at least 1 hour.

14. The process of claim 13 which further includes a dealumination step comprising contacting the mordenite zeolite with steam at a temperature of at least 200° C. for a duration of at least one hour, and then washing with an aqueous acid solution.

* * * * *